United States Patent [19]

Hunter et al.

[11] Patent Number: 5,406,828

[45] Date of Patent: Apr. 18, 1995

[54] METHOD AND APPARATUS FOR PRESSURE AND LEVEL TRANSMISSION AND SENSING

[75] Inventors: Robert M. Hunter; Frank M. Stewart, both of Bozeman, Mont.

[73] Assignee: Yellowstone Environmental Science, Inc., Bozeman, Mont.

[21] Appl. No.: 153,178

[22] Filed: Nov. 16, 1993

[51] Int. Cl.[6] ............................................. G01F 1/36
[52] U.S. Cl. .................................................. 73/4 R
[58] Field of Search ................. 73/4 R, 747, 749, 750, 73/861.52, 861.63, 861.64, 215

[56] References Cited

U.S. PATENT DOCUMENTS

| | | |
|---|---|---|
| 2,557,548 | 12/1951 | Vetter . |
| 2,604,778 | 7/1952 | Marquardt . |
| 2,668,438 | 2/1954 | Marquardt . |
| 2,755,669 | 7/1956 | Beard . |
| 3,380,463 | 4/1968 | Trethewey . |
| 3,399,573 | 9/1968 | Ponsar . |
| 3,460,394 | 8/1969 | Cryer . |
| 3,613,456 | 10/1971 | Hoppe et al. . |
| 3,620,085 | 11/1971 | Khoi . |
| 3,924,612 | 12/1975 | Dempster et al. ................. 128/2.08 |
| 4,307,609 | 12/1981 | Rosenblum . |
| 4,315,520 | 6/1982 | Atkinson et al. . |
| 4,367,652 | 1/1983 | Venuso ................................ 73/861 |
| 4,388,827 | 6/1983 | Palmer et al. . |
| 4,393,705 | 7/1983 | Eidshun . |
| 4,419,893 | 12/1983 | Baillie et al. . |
| 4,476,707 | 10/1984 | Burns et al. .......................... 73/4 R |
| 4,485,675 | 12/1984 | Verret . |
| 4,526,035 | 7/1985 | Auchapt et al. . |
| 4,571,997 | 2/1986 | Kepple et al. ........................ 73/215 |
| 4,625,548 | 12/1986 | Charter . |
| 4,669,308 | 6/1987 | Jorritsma . |
| 4,711,127 | 12/1987 | Hafner . |
| 4,719,799 | 1/1988 | Wicks et al. . |
| 4,869,104 | 9/1989 | Saito et al. . |
| 4,879,912 | 11/1989 | Suckow ............................. 73/861.61 |
| 4,949,572 | 8/1990 | Wilen et al. . |
| 5,020,368 | 6/1991 | Evans et al. . |
| 5,052,222 | 10/1991 | Stoepfel . |

OTHER PUBLICATIONS

Hager, W. H., Venturi Flume of Minimum Space Requirements, J. Irrigation & Drainage Engr., v. 114(2), 226–243, 1988.

Kilpatrich et al., Development and Testing of Highway Storm-Sewer Flow Measurement and Recording System, U.S.G.S. Water-Resources Investigations Report 85-4111, 1985.

Dedrick & Clemmens, Double-Bubblers Coupled with Pressure Transducers for Water Level Sensing, Trans. ASAE, 779–783, 1984.

Dedrick & Clemmens, Instrumentation for Monitoring Water Levels, Proceedings of the Agri-Mation 2 Conference & Exposition, Mar. 3–5, Chicago, Illinois, p. 148, 1986.

*Primary Examiner*—Richard E. Chilcot, Jr.
*Assistant Examiner*—Harshad Patel

[57] ABSTRACT

This invention provides a method and apparatus for transmitting and sensing liquid pressure (head) and liquid level (depth) in flow metering, tide gauge and liquid salinity or slurry density measurement applications. The invention essentially eliminates the effect of pressure sensor temperature variations and the effect of long-term pressure sensor signal drift on pressure sensing accuracy by resetting the zero and gain of the pressure sensor prior to pressure measurement. A variety of sources of a known differential pressure may be used to reset the gain of the differential pressure sensor by simultaneously exposing both sides of the differential pressure sensor to the known differential pressure. In one embodiment of the invention, the head loss through exhaust port of a spring-biased comparitor is the known pressure differential used to reset the pressure sensor gain. In another embodiment, a U-tube manometer is used to set a known differential pressure across an adjustable differential pressure regulator or an adjustable spring-biased comparitor and that pressure differential is used. The invention provides accurate bubbler pressure measurement under conditions of rapidly varying liquid head by means of a single calibration of a differential pressure sensor instead of sequential calibrations of a gauge pressure sensor. The present invention provides a compact and lightweight manifold-mounted pneumatic integrated circuit and a method for in situ recalibration of relatively inexpensive pressure sensors.

15 Claims, 5 Drawing Sheets

METHOD AND APPARATUS FOR PRESSURE AND LEVEL TRANSMISSION AND SENSING

STATEMENT AS TO RIGHTS IN INVENTIONS MADE UNDER FEDERALLY-SPONSORED RESEARCH AND DEVELOPMENT

This invention was made with Government support under Grant No. 92-33610-7212 awarded by the U.S. Department of Agriculture. The Government has certain rights in the invention.

BACKGROUND OF THE INVENTION

The background of the invention is set forth in two parts: the field of the invention and the description of related art.

1. Field of the Invention

This invention relates to a method and apparatus for pressure and level transmission and sensing. In particular, it relates to a method and apparatus for transmitting and sensing liquid pressure (head) and liquid level (depth) in flow-metering, tide gauge, and liquid or slurry density-measurement applications.

2. Description of Related Art

Accurate and reliable (stable) measurement of liquid pressure (head) and/or liquid level over a wide temperature range and over an extended period of time is required in a variety of applications. Flow metering applications typically comprise a primary flow metering element or device and a secondary flow metering element or device. The primary flow metering element is a constriction that causes there to be a unique relationship between liquid pressures and/or liquid levels and the flow rate. The secondary flow metering element typically accomplishes three functions: (1) measuring the pressures and/or levels produced by the primary element, (2) converting these measurements into flow rate data, and (3) recording the flow rate data.

A variety of constrictions are incorporated into primary elements. For the purposes of this disclosure, the term "constriction" means a reduction in the cross-sectional area of a conduit. The reduction may be gradual or abrupt. An example is given by W. H. Hager in "Venturi Flume of Minimum Space Requirements" in *Journal of Irrigation and Drainage Engineering*, Vol. 114, No. 2, May, 1988, p. 226, which example comprises "sharp-edged constriction plates placed symmetrically in a rectangular channel." Yet another example is given in U.S. Pat. No. 4,571,997 by Kepple et al., Feb. 25, 1986, which example comprises a metering insert that has been commercialized under the trade name "Flowpoke". Another example is given by F. A. Kilpatrich, W. R. Kaehrle, J. Hardee, E. H. Cordes and M. N. Landers in *Development and Testing of Highway Storm-Sewer Flow Measurement and Recording System*, U.S. Geological Survey Water-Resources Investigations Report 85-4111, 1985, which example comprises a Palmer-Bowlus flume installed in a closed conduit.

In open-channel flow metering, accurate measurement of the water levels upstream and downstream from the primary flow metering element (e.g., flume or weir) is necessary. For example, a water level measurement accuracy of ±3 millimeters (mm) of water is generally required for accurate flow metering of flow rates of 0.4 cubic meters per second (14 cubic feet per second) or less. In closed conduit flow metering, accurate measurement of pressures (heads) in the inlet and in the throat and/or outlet of the primary flow element (e.g., venturi tube or orifice) is required.

In tide gauge applications, accurate and stable measurement of water level is required. The U.S. National Ocean Service, for example, has indicated that it wants to be able to gauge tidal variations with an accuracy of ±3 mm and an annual stability of ±3 mm. Moreover, a production cost of the sensor (without the data recording system) should be $1,000 or less (in 1991 U.S. dollars).

Bubbler-type systems have also been used to measure density or salinity. The differential pressure (p) between two bubbler discharge ports located a known vertical distance (h) apart is used to determine the average density (w) of the liquid between the ports. The average density of the fluid between the bubbler discharge ports is given by the formula: $w = p/h$.

A variety of techniques have been used to measure water level or head at a point in a liquid, but none is both low in cost and accurate. Microwave technology can be used to sense water level with an accuracy of ±25 mm. Ultrasound technology can be used to sense water level within accuracy of ±0.25 percent of full scale (F.S.) or ±5 mm, whichever is greater. Capacitance technology can be used to sense water level with an accuracy to ±1-2 percent of F.S.

A variety of bubbler-type pressure transmitting and sensing systems have been disclosed in prior art references. Bubbler-type systems for level sensing are disclosed in U.S. Pat. Nos. 3,620,085 by Khoi, Nov. 16, 1971; 4,526,035 by Auchapt et al., Jul. 2, 1985; 4,625,548 by Charter, Dec. 2, 1986; 4,711,127 by Hafner, Dec. 8, 1987; 4,719,799 by Wicks et al., Jan. 19, 1988; 4,869,104 by Saito et al., Sep. 26, 1989 and 5,052,222 by Stoepfel, Oct. 1, 1991. Bubbler-type systems for density sensing are disclosed in U.S. Pat. Nos. 2,557,548 by Vetter, Dec. 4, 1951; 2,604,778 by Marquardt, Jul. 29, 1952; 2,668,438 by Marquardt, Feb. 9, 1954; 2,755,669 by Beard, Jul. 24, 1956; 3,380,463 by Trethewey, Apr. 30, 1968; 3,399,573 by Ponsar, Sep. 3, 1968; 3,460,394 by Cryer, Aug. 12, 1969; 3,613,456 by Hoppe et al., Oct. 19, 1971; 4,307,609 by Rosenblum, Dec. 29, 1981; 4,393,705 by Eidshun, Jul. 19, 1983; 4,419,893 by Baillie et al., Dec. 13, 1983; 4,485,675 by Verret, Dec. 4, 1984; 4,949,572 by Wilen et al., Aug. 21, 1990 and 5,020,368 by Evans et al., Oct. 1, 1991. Bubbler-type systems for flow metering are disclosed in U.S. Pat. Nos. 4,367,652 by Venuso, Jan. 11, 1983; 4,388,827 by Palmer et al., Jun. 21, 1983 and 4,669,308 by Jorritsma, Jun. 2, 1987.

Bubbler-type pressure transmitting and sensing systems are also disclosed by A. R. Dedrick and A. J. Clemmens in "Double-Bubblers Coupled with Pressure Transducers for Water Level Sensing" in *Transactions of the ASAE*, 1984, p. 779, and A. R. Dedrick and A. J. Clemmens in "Instrumentation for Monitoring Water Levels" in *Proceedings of the Agri-Mation TM 2 Conference & Exposition*, Mar. 3-5, 1986, Chicago, Ill., p. 148. These systems implement the "double-bubbler" concept in which the pressure in two bubbler tubes is determined sequentially by means of a gauge pressure sensor referenced to atmospheric pressure. The ends of the bubbler tubes are submerged in water and are located a known vertical distance apart in fresh water. The difference between the two sequential pressure measurements comprises a known head that is used to calibrate the gain (span) of the pressure sensor. In that the gauge pressure sensor can be zeroed by venting its pressure port to atmospheric pressure, both the offset and span of the sensor can be recalibrated prior to use of the pressure sensor to measure the unknown pressure in one of the bubbler tubes. Limitations of this system include the time required for sequential exposure of a gauge pressure sensor to the pressures in two different bubbler circuits to reset gain and incorporation of bulky and heavy needle valves and differential pressure regulators into the system.

SUMMARY OF THE INVENTION

The present invention provides a method and apparatus for pressure and level transmission and sensing. The method and apparatus overcome the limitations of prior art means for pressure and level transmission and sensing. With the present invention, the pressure(s) at the end of one or more bubbler tubes (means for discharging bubbles) is transmitted to one or more relatively inexpensive differential pressure sensors (e.g., transducers) having a relatively linear response to pressure changes. Differential pressure sensors have both a pressure port (or side) and a reference port (or side). In preferred embodiments, the pressure sensor(s) are recalibrated prior to each pressure or level measurement or somewhat less frequently. In this way, the sensor(s) are not subject to temperature or drift (stability) errors.

The invention can be used to transmit and sense a single pressure (head) or level (depth) or to transmit and sense a plurality of pressures or levels. In one embodiment, a single depth is monitored using an apparatus comprising a double-bubbler system and a single differential pressure sensor. The bubbler system comprises a source of compressed gas (such as an air compressor or a cylinder of compressed nitrogen), two bubbler circuits, and a pair of orifices (or needle valves) and adjustable spring-biased comparitors (or differential pressure regulators) for regulating the flow rate of the compressed gas into each bubbler circuit, and a differential pressure sensor. The adjustable spring-biased comparitors may be of the type that incorporates the fluid leak-port orifice structure disclosed in U.S. Pat. No. 4,315,520 by Atkinson et al., Feb. 16, 1982, the disclosure of which is incorporated by reference herein.

The bubbler circuits discharge (release bubbles) through ports having a fixed and known difference in elevation, preferably with the second bubbler circuit discharging at the lower elevation. The differential pressure sensor has a pressure side and a reference side. Valves (preferably solenoid valves) and pneumatic circuitry are provided that allow (1) the reference side to be exposed to atmospheric pressure while the pressure side is exposed to atmospheric pressure and/or (2) the reference side and the pressure side to be simultaneously exposed to the same relatively constant pressure (which may be different from ambient atmospheric pressure). The valves and circuitry also allow the reference side to be exposed to the pressure in the first (i.e., lower pressure) bubbler circuit and the pressure side to be simultaneously exposed to the pressure in the second (i.e., higher pressure) bubbler circuit.

At the beginning of a selected (or each) measurement cycle, the pressure sensor "zero" is reestablished by exposing both sides of the sensor simultaneously to the same pressure. This can be the pressure in one of the bubbler circuits or ambient atmospheric pressure. Computer means are used to reset the zero signal of the pressure sensor. In this way, errors caused by temperature variation and signal drift over time on the sensor zero signal are eliminated.

After the sensor zero is reestablished, the pressure side of the sensor is connected to the higher pressure bubbler circuit (that circuit discharging through the port at the lower elevation) and the reference side of the sensor is simultaneously connected to the lower pressure bubbler circuit. Computer means use this known pressure differential to reset the span or gain of the pressure sensor. In this way, errors caused by temperature variation and signal drift over time on the sensor span or gain signal are eliminated.

The depth of liquid over the lower elevation bubbler port can then be accurately determined. Bubbles are released from the lower port and the pressure in the second bubbler circuit is sensed by the differential pressure sensor. Computer means are used to convert the pressure signal to units of head.

A variety of sources of a known differential pressure may be used to reset the gain of the differential pressure sensor by simultaneously exposing both sides of the differential pressure sensor to the known differential pressure. For example, in the best mode of the invention, the head loss through the exhaust port of a spring-biased comparitor is the known pressure differential used to reset the pressure sensor gain. In another embodiment, a U-tube manometer is used to set a known differential pressure across an adjustable differential pressure regulator or an adjustable spring-biased comparitor, and that known pressure differential is used to reset the pressure sensor gain. In another embodiment, one side of a U-tube manometer is pressurized to create a known pressure and the difference between that pressure and atmospheric pressure is used.

The invention may also be used to transmit and sense a plurality of pressures or liquid levels instead of a single pressure or level. In these embodiments, the apparatus for transmission and sensing of pressures comprises the following elements:

a source of compressed gas, a plurality of bubbler circuits connected to said source of compressed gas, means for controlling bubble release rate, one said means for controlling associated with each bubbler circuit, means for releasing a plurality of bubbles of said gas connected to each bubbler circuit, said plurality of bubbles being exposed to said pressures, at least one means for sensing differential pressure connected to said plurality of bubbler circuits, said means for sensing having a pressure side and a reference side, and said means for sensing producing a plurality of signals when excited and having an offset and a gain, means for simultaneously applying a single pressure to the pressure side and the reference side of said means for sensing differential pressure to produce a zero pressure signal, means for determining the offset of and for zeroing said means for sensing differential pressure by reference to at least said zero pressure signal.

The apparatus may further comprise the following elements:

means for generating a known pressure that is different from atmospheric pressure, means for simultaneously imposing said known pressure across said means for sensing differential pressure to produce a known pressure signal, and means for recalibrating the gain of said means for sensing differential pressure by reference to at least one said known pressure signal.

The invention has a variety of applications. In one embodiment of the invention, the apparatus further comprises a primary flow metering element comprising a constriction in a pipeline. The constriction comprises a weir or an orifice which may be of any shape and may be variable in area. A first bubble-releasing port is exposed to the pressure upstream from the weir or orifice and a second bubble-releasing port is exposed to the pressure downstream from the weir or orifice. Computer means are used to convert the pressure signals to flow rate data.

In another embodiment of the invention, the apparatus further comprises a constriction in a pipeline that is a flume. The flume may be a venturi flume or a modified (critical depth) venturi flume. The flume may or may not have a throat. A first means for releasing bubbles is exposed to the pressure upstream from the flume and a second means for releasing bubbles is exposed to the pressure downstream from said flume. Computer means are used to convert the pressure signals to flow rate data.

In another embodiment, the apparatus further comprises a flume having a throat of finite length. A first means for releasing bubbles is exposed to the pressure upstream from the flume throat and a second means for releasing bubbles is exposed to the pressure downstream in the flume throat. Computer means are used to convert the pressure signals to flow rate data.

In another embodiment, the means for releasing bubbles is a bubbler-type water-level or tide gauge. At least one bubble-releasing port is situated below the lowest water level. Computer means are used to convert the pressure signals to water surface data.

In another embodiment, the means for releasing bubbles is a bubbler-type slurry or liquid density or salinity gauge. At least two bubble-releasing ports are situated a known vertical distance apart below the surface of a liquid or slurry of unknown density or salinity. Computer means are used to convert the pressure signals to density data.

The present invention provides a variety of advantages over the prior art. One object of the invention is to essentially eliminate the effect of pressure sensor temperature variations on pressure sensing accuracy. Another object of the invention is to essentially eliminate the effect of long-term drift in pressure sensor zero (offset) and gain on pressure sensing accuracy. Another object of the invention is to provide meter users with another choice of pressure transmitting and sensing techniques. This is important to users who, for whatever reason, prefer the bubbler technique to others (e.g., the submersible pressure transducer technique) for pressure transmission and sensing.

An object of the invention is accurate pressure measurement under conditions of rapidly varying liquid head by means of a single calibration of a differential pressure sensor instead of sequential calibrations of a gauge pressure sensor. It is an object of the invention to provide a means for generating a fixed, known pressure difference that is portable and stable. It is an object of some embodiments of the invention to provide a plurality of means for discharging bubbles and a plurality of means for generating known pressure differences. It is an object of the invention to allow manual or automatic selection of the appropriate means for generating a pressure difference of known magnitude, said known magnitude depending on the magnitude of the pressure being sensed. It is an object of some embodiments of the invention to control the pressure of the source of compressed gas by reference to the pressure in at least one of the means for discharging bubbles. It is a further objective of the invention to provide a zero pressure differential and known, non-zero pressure differential for calibration of bubble-type density sensors.

The present invention provides a compact and lightweight method for recalibration of relatively inexpensive pressure sensors. Further objects and advantages of the invention will become apparent from consideration of the drawings and the ensuing description of it.

BRIEF DESCRIPTION OF THE DRAWINGS

The features of the invention will be better understood by reference to the accompanying drawings which illustrate presently preferred embodiments of the invention.

In the drawings.

The following reference numerals are used to indicate the parts of the invention on the drawings:

1 apparatus for pressure and level transmission and sensing
2 compressor, air pump, or source of compressed gas
4 first balancing orifice
6 second balancing orifice
8 third balancing orifice
10 first solenoid valve
12 second solenoid valve
14 third solenoid valve
16 first adjustable spring-biased comparitor
18 second adjustable spring-biased comparitor
20 third adjustable spring-biased comparitor
22 fourth orifice
24 fifth orifice
26 sixth orifice
28 seventh orifice
40 fourth solenoid valve
42 fifth solenoid valve
44 sixth solenoid valve
46 first bubbler port, first bubble-releasing port or first means for releasing bubbles
48 second bubbler port, second bubble-releasing port or second means for releasing bubbles
50 third bubbler port
52 first bubbler circuit
54 second bubbler circuit
56 third bubbler circuit
60 seventh solenoid valve
62 first differential pressure sensor
64 eighth solenoid valve
66 second differential pressure sensor
70 atmosphere -continued

| | |
|---|---|
| 72 | gauge pressure sensor |
| 80 | ninth solenoid valve |
| 84 | U-tube manometer |
| 90 | pneumatic integrated circuit |
| 92 | manifold |
| 100 | first flow meter |
| 102 | first primary flow metering element |
| 104 | first constriction |
| 106 | pipeline |
| 108 | weir or orifice |
| 110 | computer means |
| 120 | second flow meter |
| 122 | second constriction |
| 124 | first flume |
| 150 | third flow meter |
| 152 | second flume |
| 154 | throat |
| 160 | tide gauge |
| 162 | lowest expected water surface elevation |
| 164 | datalogger/controller |
| 200 | density sensor |
| 202 | plurality of bubbles |
| 210 | first layer |
| 212 | second layer |
| 214 | 214 third layer |

DESCRIPTION OF THE PREFERRED EMBODIMENTS

Figure 1:
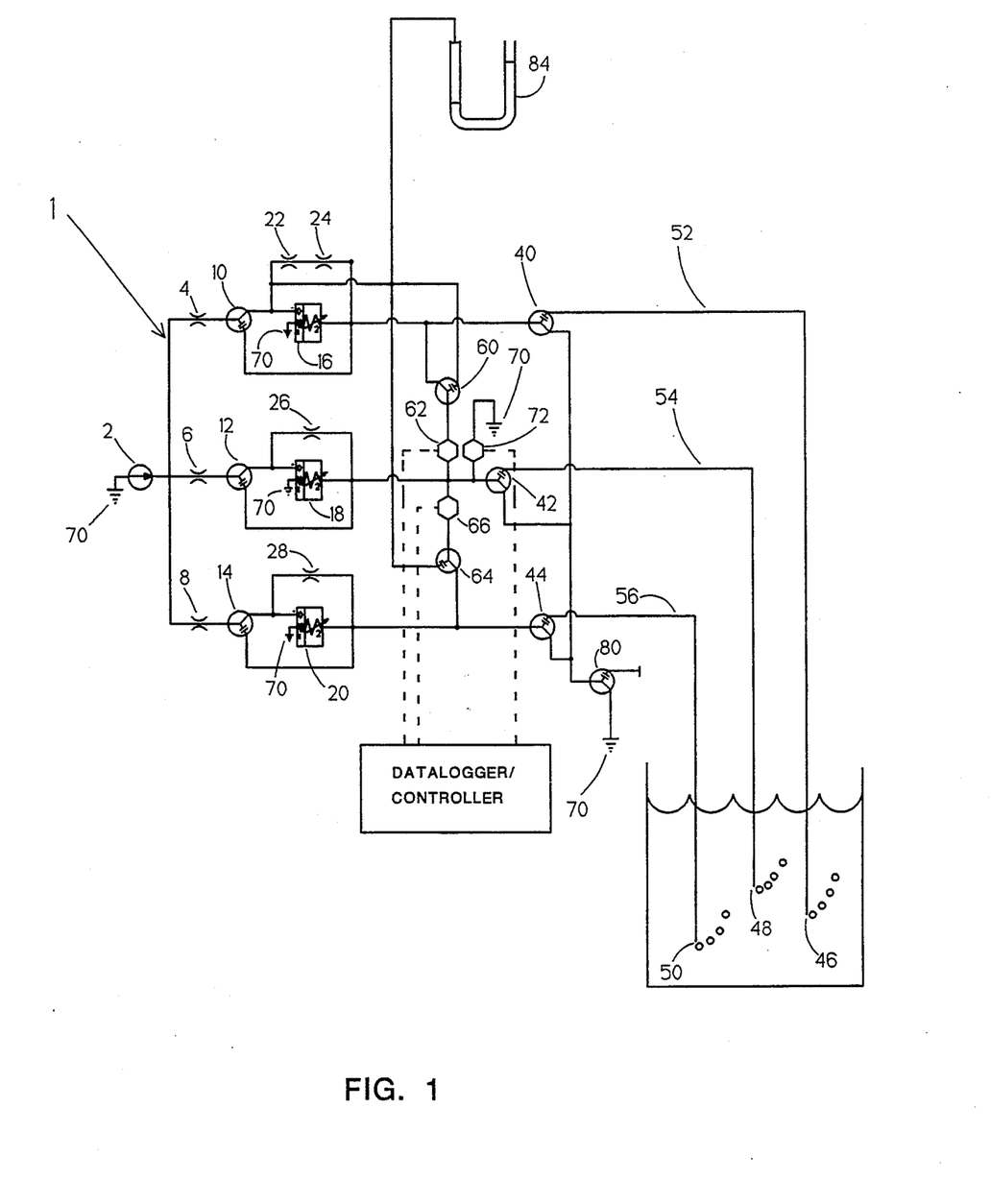
FIG. 1 is a highly schematic pneumatic diagram of the apparatus for pressure and level transmission and sensing.

Reference is now made to FIG. 1 which is a highly schematic pneumatic diagram of a representative embodiment of apparatus for pressure and level transmission and sensing 1. This embodiment is capable of measuring two differential pressures and one gauge pressure. Compressor or air pump 2 provides compressed gas by removing air from the ambient atmosphere 70 and pressurizing it. Compressed air flows through first 35 balancing orifice 4, second balancing orifice 6 and third balancing orifice 8. These orifices ensure that relatively similar air flow rates occur in each bubbler circuit during simultaneous purging of all circuits.

Solenoid valves 10, 12, 14, 40, 42, 44, 60, 64, and 80 are three way valves. Said valves have an open air passage between the common port and normally open port when they are deactivated (no electrical power applied), and an open air passage between the common port and the normally closed port when they are activated (electrical power applied).

During normal bubbling operations, electrical power is applied to activate compressor 2, fourth solenoid valve 40, fifth solenoid valve 42, and sixth solenoid valve 44. The remaining solenoid valves 10, 12, 14, 60, 64, and 80 are deactivated. Compressed air flows in parallel through (1) first balancing orifice 4, first solenoid valve 10, first adjustable spring-biased comparitor 16 and forth orifice 22 and fifth orifice 24, (2) second balancing orifice 6, second solenoid valve 12, second adjustable spring-biased comparitor 18 and sixth orifice 26, and (3) third balancing orifice 8, third solenoid valve 14, third adjustable spring-biased comparitor 20 and seventh orifice 28. Flow in parallel through each adjustable spring-biased comparitor and orifice (or orifice pair) maintains the bubble rate in each circuit relatively constant over a wide range of pressures in each circuit.

In some embodiments (not shown), a receiver (tank) pressurized to a fixed differential pressure above the pressure in one of the bubbler circuits is used to control bubble rate in all bubbler circuits. The fixed pressure differential is maintained by a compressor activated by means of a pressure switch (not shown) on the tank referenced to pressure in the bubbler circuit.

Compressed air flows through fourth solenoid valve 40 into the portion of the first bubbler circuit 52 leading to first bubbler port 46 that discharges a plurality of bubbles 202. Similarly, air flowing through fifth solenoid valve 42 discharges into the portion of second bubbler circuit 54 that discharges a plurality of bubbles 202 through second bubbler port 48 and air flowing through sixth solenoid valve 44 discharges into the portion of third bubbler circuit 56 that discharges a plurality of bubbles 202 through third bubbler port 50. Because bubble air flow rates are very low, essentially no head loss occurs in each bubbler circuit. Moreover, the head losses can be kept essentially equal if the tubing segments used in the bubbler circuits are equal in diameter and length.

The differential pressure between first bubbler circuit 52 and second bubbler circuit 54 is transmitted to and sensed by first differential pressure sensor 62. Similarly, the differential pressure between third bubbler circuit 56 and second bubbler circuit 54 is transmitted to and sensed by second differential pressure sensor 66. The gauge pressure in second bubbler circuit 54 is transmitted to and sensed by gauge pressure sensor 72 which is referenced to the pressure in the atmosphere 70.

In an alternative embodiment (not shown), wherein the bubble discharge ports are located significant distances from the pressure sensors, different tubes can be used to convey air to discharge ports from those tubes in which pressures are sensed. In this way, the head losses associated with air movement through the bubbler circuit tubes over long distances are not added to the pressures existing at the discharge ports.

During the time intervals between measurements, all of the solenoid valves (10, 12, 14, 40, 42, 44, 60, 64, and 80) and the compressor 2 are deactivated. Any water which is forced into first bubbler circuit 52 between measurements is blocked by deactivated forth solenoid valve 40. Similarly, water in second bubbler circuit 54 is blocked by fifth solenoid valve 42, and water in third bubbler circuit 56 is blocked by sixth solenoid valve 44.

Resetting of the zeros (offsets) of the pressure sensors is accomplished by simultaneously exposing both sides of each pressure sensor to atmospheric pressure. This is accomplished by deactivating all solenoid valves and compressor 2. After the pressure in the first and second bubbler circuits bleeds out through the exhaust port of first adjustable spring-biased comparitor 16, both sides of all three pressure sensors are exposed to atmospheric pressure. After the zeros are reset, the electrical signals produced by each pressure sensor are indicative of zero pressure.

In some embodiments, the gain of first differential pressure sensor 62 and second differential pressure sensor 66 are intermittently reestablished. In a preferred embodiment, this is accomplished by deactivating fourth solenoid valve 40, fifth solenoid valve 42, sixth solenoid valve 44 and ninth solenoid valve 80, and activating compressor 2, seventh solenoid valve 60 and eighth solenoid valve 64. This simultaneously exposes the pressure sides of both pressure sensors to the pressure upstream from first adjustable spring-biased comparitor 16 and the reference side of both pressure sensors to atmospheric pressure. This known pressure differential is used to reestablish the gain (span) of the pressure sensors. In some embodiments, this pressure differential can be manually reset at regular intervals (e.g., weeks or months) by adjusting adjustable spring-biased comparitor by reference to U-tube manometer 84. The datalogger/controller 164 can then be programmed to automatically reset both offset and gain prior to each pressure measurement.

In other embodiments, the pressure sensors are temperature compensated by means of internal circuitry. In these embodiments, intermittent automatic resetting of the zero signals of the pressure sensors is sufficient to maintain pressure sensing accuracy. An example of a temperature-compensated differential pressure sensor is Motorola Model MPX2052D.

In some embodiments, the head loss produced by the adjustable spring-biased comparitor or the spring-biased differential pressure regulator varies with the temperature of the apparatus. The known differential head at any temperature can be established by developing an algorithm or curve that relates head loss to apparatus temperature. An algorithm that is appropriate for use with Airtrol Model 4104-10 spring-biased comparitors to calculate a known differential head in millimeters (mm) of water is as follows:

$$KDH = SH - 0.324 * T$$

where
- KDH = known differential head, mm of water
- S = differential head set across the comparitor at 0° C., mm of water
- T = temperature in degrees C.

In other embodiments, the variation in head loss with temperature is eliminated by incorporating springs fabricated from an alloy having a constant modulus of elasticity over a wide temperature range, such as Elinvar, Iso-Elastic, Elgiloy, Ni-Span C Alloy 902, Elinvar Extra, or Precision C into the spring-biased comparitor or differential pressure regulator.

Figure 2:
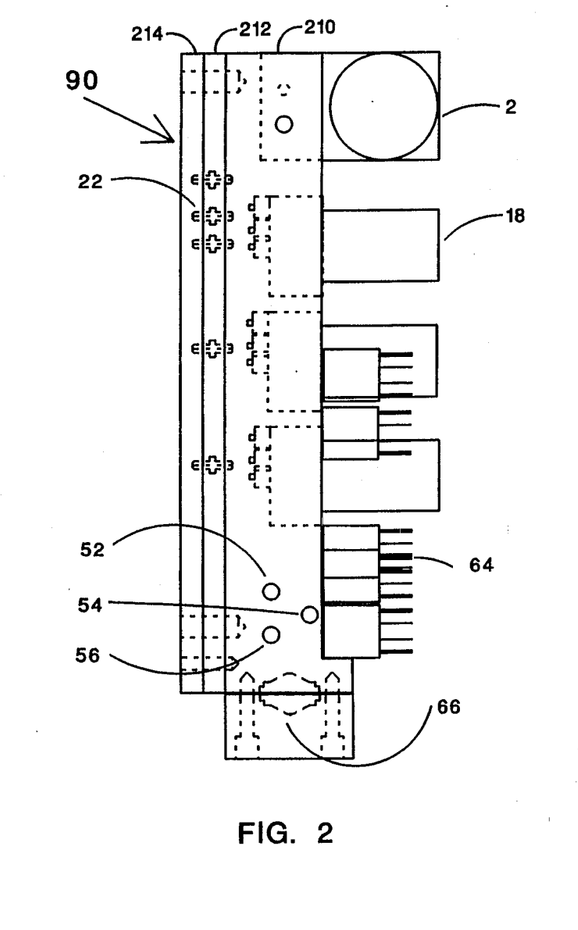
FIG. 2 is a plan view of the pneumatic integrated circuit.
Figure 3:
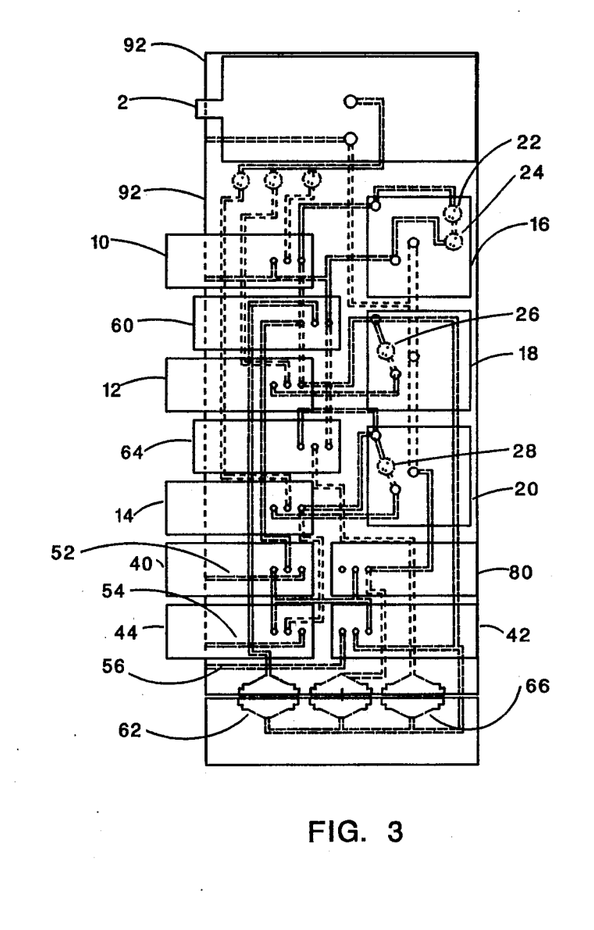
FIG. 3 is an elevation view of the pneumatic integrated circuit.

Referring to FIGS. 2 and 3, a presently preferred embodiment of the invention is presented. Pneumatic integrated circuit 90 comprises a plurality of the elements of the invention mounted on and within manifold 92. For the purposes of this disclosure, the term "manifold" means a component having a chamber with a plurality of outlets through which a gas is distributed. Mounted on and within manifold 92 is source of compressed gas 2, first, second and third bubbler circuits 52, 54, and 56 connected to source of compressed gas 2, and means for controlling bubble release rate, comprising first adjustable spring-biased comparitor 16 and fourth and fifth orifices 22 and 24, second adjustable spring-biased comparitor 18 and sixth orifice 26, third adjustable spring-biased comparitor 20 and seventh orifice 28. One means for controlling bubble rate is associated with each bubbler circuit. Two means for sensing differential pressure, differential pressure sensors 62 and 66, are connected to the bubbler circuits. Differential pressure sensors 62 and 66 each have a pressure side and a reference side, and produce electrical signals proportional to differential pressure when excited.

Fourth solenoid valve 40, fifth solenoid valve 42, sixth solenoid valve 44, seventh solenoid valve 60, eighth solenoid valve 64, and ninth solenoid valve 80 provide means for simultaneously applying a single pressure to the pressure side and the reference side of said means for sensing differential pressure to produce a zero pressure signal. Fourth solenoid valve 40 and sixth solenoid valve 44, activating fifth solenoid valve 42, seventh solenoid valve 60, eighth solenoid valve 64, ninth solenoid valve 80, and compressor 2 provide means for generating a known pressure that is different from atmospheric pressure, and means for simultaneously imposing said known pressure across said means for sensing differential pressure to produce a known pressure signal.

Means for bypassing the spring biased compressors 16, 18, and 20 are provided respectively by first solenoid valve 10, second solenoid valve 12, and third solenoid valve 14. Bypassing the said spring biased comparitors provides a relatively high air flow rate in order to purge bubble circuits 52, 54, and 56.

In the embodiment shown in FIGS. 2 and 3, manifold 92 is comprised of first layer 210, second layer 212 and third layer 214. The portions of first, second, and third bubbler circuits 52, 54, and 56 within manifold 92 may be formed, in part, by machining channels in at least second layer 212 and third layer 214 and by drilling holes in at least first layer 210 and second layer 212. In this embodiment, the layers are held together and pneumatic separation of the channels is ensured by a layer of cement between each pair of layers. Maintenance of manifold 92 is facilitated by using as the cement, Sashco Lexel, which cement can be removed by soaking manifold in kerosene, thereby allowing manifold 92 to be disassembled.

In other embodiments, the portions of first, second and third bubbler circuits 52, 54, and 56 within manifold 92 are formed, in part by providing a first compressible gasket (not shown) between first layer 210 and second layer 212 and a second compressible gasket (not shown) between second layer 212 and third layer 214. Channels are formed in the first and second compressible gaskets by injection molding or other conventional methods. In this embodiment, the layers can be held together with removable bolts.

Figure 4:
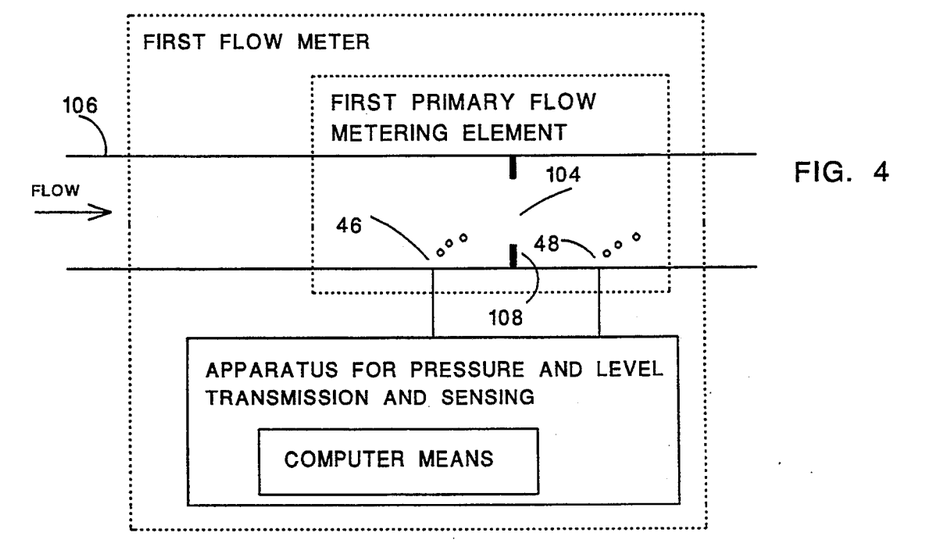
FIG. 4 is a highly schematic representation of a first flow metering application of the invention.

Referring to FIG. 4, a highly schematic representation of a first flow-metering application of the invention is presented. In this embodiment of the invention, the first flow meter 100 comprises apparatus for pressure and level transmission and sensing 1 and first primary flow metering element 102 comprising first constriction 104 in pipeline 106. First constriction 104 is formed by weir or orifice 108, which constriction may be of any shape and may be variable in area. A flow meter with a variable area orifice is sometimes termed a "variable gate" flow meter (Isco, Inc., Lincoln, Nebr.). First bubble-releasing port 46 is exposed to the pressure upstream from weir or orifice 108 and second bubble-releasing port 48 is exposed to the pressure downstream from weir or orifice 108. Computer means 110 are used to convert the pressure signals to flow rate data.

Figure 5:
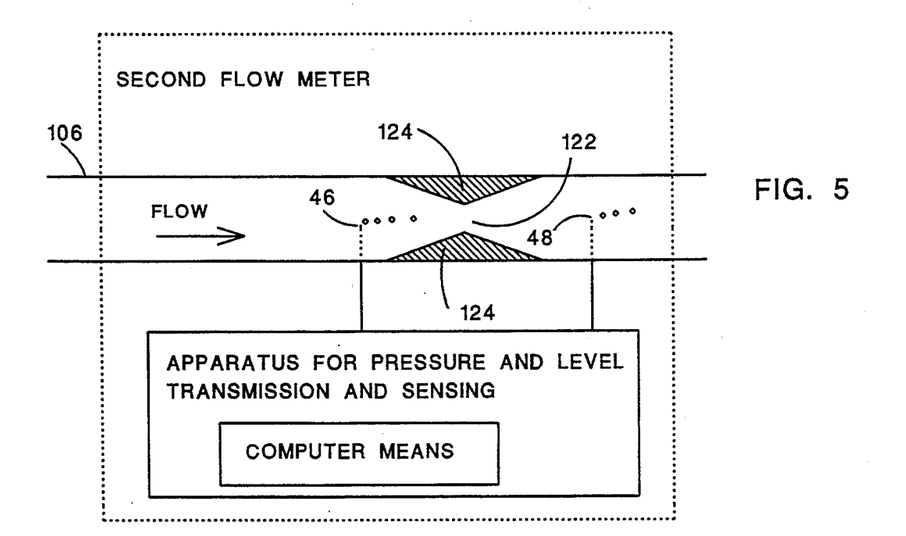
FIG. 5 is a highly schematic representation of a second flow metering application of the invention.

Referring to FIG. 5, a highly schematic representation of a second flow metering application of the invention is presented. In this embodiment of the invention, second flow meter 120 comprises apparatus for pressure and level transmission and sensing 1 and second constriction 122 in a pipeline 106 that is first flume 124. First flume 124 may be a venturi flume or a modified (critical depth) venturi flume. In the embodiment shown, first flume 124 has a throat of finite length. First means for releasing bubbles 46 is exposed to the pressure upstream from first flume 124 and second means for releasing bubbles 48 is exposed to the pressure downstream from first flume 124. Computer means 110 are used to convert the pressure signals to flow rate data.

Figure 6:
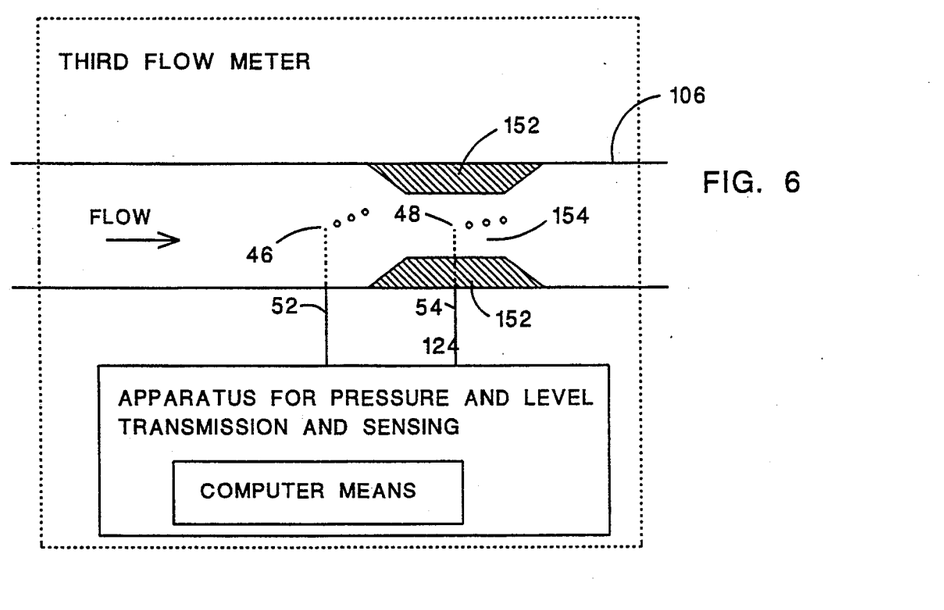
FIG. 6 is a highly schematic representation of a third flow metering application of the invention.

Referring to FIG. 6, a highly schematic representation of a third flow metering application of the invention is presented. In this embodiment, third flow meter 150 comprises apparatus for pressure and level transmission and sensing 1 and second flume 152 having throat 154 of finite length in pipeline 106. First means for releasing bubbles 46 is exposed to the pressure upstream from the throat 154 and second means for releasing bubbles 48 is exposed to the pressure in throat 154. Computer means 110 are used to convert the pressure signals to flow rate data.

Figure 7:
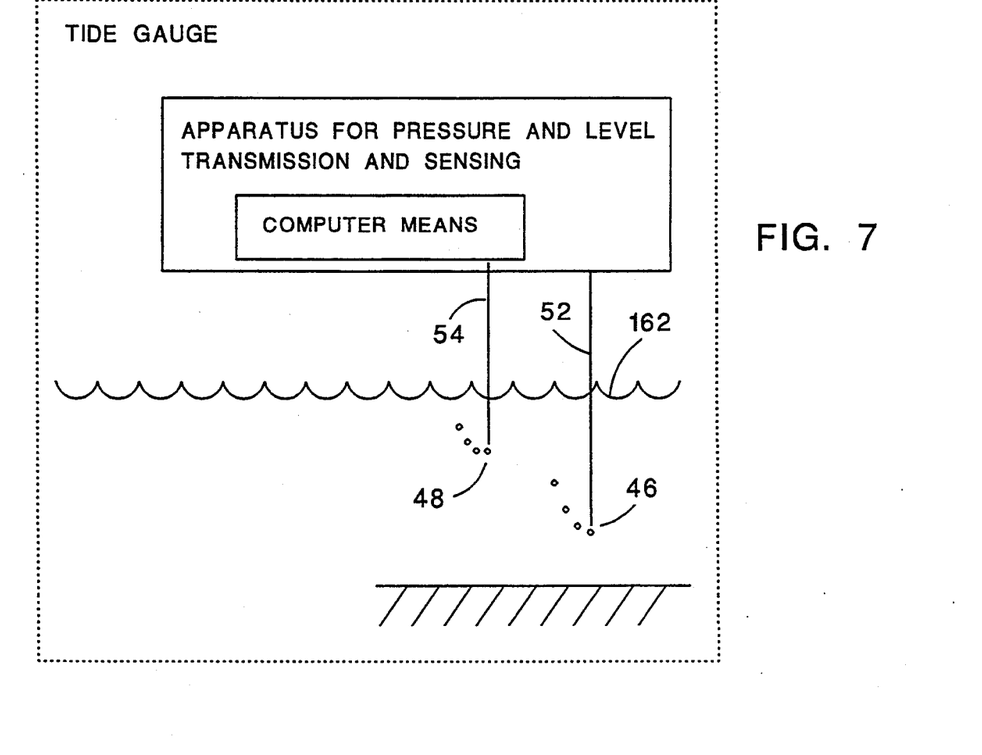
FIG. 7 is a highly schematic representation of a water level sensing application of the invention.

Referring to FIG. 7, a highly schematic representation of a water level sensing application of the invention is presented. Apparatus for pressure and level transmission and sensing 1 is incorporated into tide gauge 160. Apparatus 1 pressurizes first bubbler circuit 52 and second bubbler circuit 54. Bubbler circuit 52 discharges bubbles through bubbler port 46 and bubbler circuit 54 discharges bubbles through bubbler port 48. In this embodiment, both bubbler ports are located below lowest expected water surface elevation 162. Computer means 110 are used to convert the pressure signals to water surface data.

Figure 8:
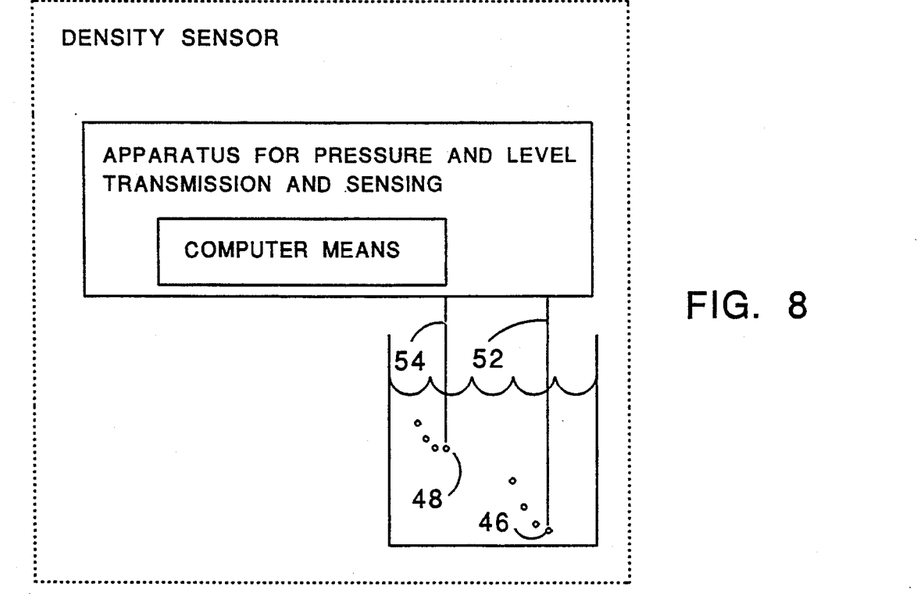
FIG. 8 is a highly schematic representation of a density sensing application of the invention.

Referring to FIG. 8, a highly schematic representation of a density-sensing application of the invention is presented. Apparatus for pressure and level transmission and sensing 1 is incorporated into density sensor 200. Apparatus 1 pressurizes first bubbler circuit 52 and second bubbler circuit 54. Bubbler circuit 52 discharges bubbles through bubbler port 46 and bubbler circuit 54 discharges bubbles through bubbler port 48. Computer means 110 are used to convert the pressure signals to density data using the formula presented above.

Many variations of the invention will occur to those skilled in the art. For example, a variety of circuit designs could be used to accomplish the steps of the invention. All such variations within the scope of the claims are intended to be within the scope and spirit of the invention.

We claim:

1. An integrated pneumatic circuit comprising a plurality of components comprising:
   a source of compressed gas,
   a plurality of bubbler circuits connected to said source of compressed gas,
   at least one means for controlling bubble release rate, one said means for controlling being associated with each said bubbler circuit,
   at least one means for sensing differential pressure connected to said plurality of bubbler circuits, said means for sensing having a pressure side and a reference side, and said means for sensing producing a plurality of signals when excited,
   means for simultaneously applying equal pressures to the pressure side and the reference side of each said means for sensing differential pressure to produce a zero pressure signal,
   means for generating a known pressure differential,
   wherein said means for generating a known pressure differential is selected from the group consisting of
      means for generating a known head and a known head loss,
      means for sensing pressures at a plurality of known elevations or depths in a liquid,
      means for sensing pressures at known elevations or depths in liquids of known density,
      means for generating a known gauge pressure that is referenced to atmospheric pressure, and
      means for generation a gas pressure that is regulated above atmospheric pressure, and
   means for simultaneously imposing said known pressure differential across each said means for sensing differential pressure to produce a known pressure signal,
   wherein the plurality of components are mounted on and within a single manifold.

2. The apparatus of claim 1 wherein said means for sensing differential pressure comprises a temperature-compensated pressure transducer.

3. An apparatus for transmission and sensing of pressures comprising:
   a source of compressed gas,
   a plurality of bubbler circuits connected to said source of compressed gas,
   means for releasing a plurality of bubbles of said gas, said means for releasing connected to each bubbler circuit, said plurality of bubbles being exposed to said pressures,
   means for controlling bubble release rate,
   at least one means for sensing differential pressure connected to said plurality of bubbler circuits, said means for sensing having a pressure side and a reference side, and said means for sensing producing a plurality of signals when excited, said plurality of signals being characterized by an offset or zero and a gain,
   means for simultaneously applying a single pressure to the pressure side and the reference side of each said means for sensing differential pressure to produce a zero pressure signal,
   means for resetting the zero of said means for sensing differential pressure by reference to at least said zero pressure signal,
   means for generating a known pressure differential,
   wherein said means for generating a known pressure differential is selected from the group consisting of
      means for generating a known head and a known head loss,
      means for sensing pressures at a plurality of known elevations or depths in a liquid,
      means for sensing pressures at known elevations or depths in liquids of known density,
      means for generating a known gauge pressure that is referenced to atmospheric pressure, and
      means for generating a gas pressure that is regulated above atmospheric pressure, and
   means for simultaneously imposing said known pressure differential across each said means for sensing differential pressure to produce a known pressure signal, and
   means for resetting the gain of said means for sensing differential pressure by reference to at least said known pressure signal.

4. The apparatus of claim 3 wherein said means for generating a known pressure comprises a pressurized manometer.

5. The apparatus of claims 3 wherein said means for releasing bubbles is a tide gauge.

6. The apparatus of claims 3 wherein said means for releasing bubbles is density gauge.

7. A method for transmission and sensing of pressures comprising:
   compressing a gas,
   connecting a plurality of bubbler circuits to a means for releasing bubbles,
   releasing bubbles of said gas, said bubbles being exposed to said pressures,
   controlling bubble release rate, sensing at least one differential pressure by means of a means for sensing differential pressure connected to said plurality of bubbler circuits, said means for sensing having a pressure side and reference side, and said means for sensing producing signals when excited, said plurality of signals being characterized by an offset or zero and a gain, simultaneously applying a single pressure to the pressure side and the reference side of each said means for sensing differential pressure to produce a zero pressure signal, resetting the zero of said means for sensing differential pressure by reference to at least said zero pressure signal, generating a known differential pressure, wherein said means for generating a known pressure differential is selected from the group consisting of means for generating a known head and a known head loss, means for sensing pressures at a plurality of known elevations or depths in a liquid, means for sensing pressures at known elevations or depths in liquids of known density, means for generating a known gauge pressure that is referenced to atmospheric pressure, and means for generating a gas pressure that is regulated above atmospheric pressure, and simultaneously imposing said known pressure differential across each said means for sensing differential pressure to produce a known pressure signal, and resetting the gain of said means for sensing differential pressure by reference to at least said known pressure signal.

8. The method of claim 7 wherein generating a known pressure is accomplished by means of a differential pressure regulator.

9. The method of claim 7 wherein generating a known pressure is accomplished by means of a pressurized manometer.

10. The method of claim 7 wherein said bubbles are exposed to pressures produced by a bubbler-type tide gauge.

11. The method of claim 7 wherein said bubbles are exposed to pressures produced by a bubbler-type density sensor.

12. The method of claim 7 further comprising purging each of the plurality of bubbler circuits in accordance with a mode operation selected from the group consisting of simultaneously purging all bubbler circuits, and sequentially purging each bubbler circuit.

13. An apparatus for transmitting and sensing the pressure head at a point in a liquid comprising a bubbler system comprising a source of compressed gas and at least a first means for discharging bubbles, at least one differential pressure sensor, said at least one differential pressure sensor having a pressure port and a reference port, means for generating a pressure difference across said at least one differential pressure sensor, said pressure difference being fixed and known, the pressure on one side of said means for generating a pressure difference being relatively higher than the pressure on the other side of said means for generating a pressured wherein said means for generating skid pressure difference is selected from the group consisting of means for generating a known head and a known head loss, and means for sensing pressures at a plurality of known elevations or depths in a liquid, and wherein at least said reference port is adapted to be exposed to atmospheric pressure, and said pressure port and said reference port are adapted to be exposed to equal pressures to produce a zero pressure signal, and wherein said reference port is adapted to be exposed to the pressure of the lower pressure side of said means for generating a pressure difference and said pressure port is adapted to be simultaneously exposed to the pressure on the one higher pressure side of said means for generating pressure to produce a signal that is characteristic of said pressure difference, and wherein said pressure port is adapted to be exposed to said first means for discharging bubbles.

14. The apparatus of claim 13 wherein said means for generating a pressure difference comprises a needle valve and a differential pressure regulator.

15. A method for transmission and sensing of pressures comprising:

transmitting a pressure to a pressure sensor by means of a bubbler circuit, measuring said pressure with said pressure sensor, said sensor having a pressure side, and a reference side, said pressure sensor producing a plurality of signals when excited, said plurality of signals being characterized by an offset or zero and a gain, resetting said offset or zero by simultaneously exposing said pressure side and said reference side to equal pressures, resetting said gain by simultaneously exposing said pressure side to a known pressure and said reference side to a different known pressure, and wherein said known pressures are generated by a means selected from the group consisting of means for generating a known head and a known head loss, means for sensing pressures at a plurality of known elevations or depths in a liquid, means for sensing pressures at known elevations or depths in liquids of known density, means for generating a known gauge pressure that is referenced to atmospheric pressure, and means for generating a gas pressure that is regulated above atmospheric pressure.

* * * * *